United States Patent [19]

Kogoma et al.

[11] 4,391,994

[45] Jul. 5, 1983

[54] PROCESS FOR THE PRODUCTION OF ETHERS

[75] Inventors: Kiyoshi Kogoma, Chiba; Yu Ohashi, Ichihara; Jiro Niizeki, Chiba; Norio Sone; Takashi Tobita, both of Ichihara, all of Japan

[73] Assignee: Nisso Petrochemical Industrie Co., Ltd., Tokyo, Japan

[21] Appl. No.: 312,781

[22] Filed: Oct. 19, 1981

Related U.S. Application Data

[63] Continuation-in-part of Ser. No. 161,930, Jun. 23, 1980, abandoned.

[30] Foreign Application Priority Data

Jul. 4, 1979 [JP] Japan .................................. 54/84686

[51] Int. Cl.$^3$ ............................................. C07C 41/02
[52] U.S. Cl. .................................... 568/593; 568/601; 568/607; 568/608; 568/609; 568/610; 568/613; 568/614

[58] Field of Search ............... 568/613, 607, 593, 601, 568/608, 609, 610, 614

[56] References Cited

U.S. PATENT DOCUMENTS 4,146,736  3/1979  Scheffel et al. ..................... 568/607

*Primary Examiner*—Bernard Helfin
*Attorney, Agent, or Firm*—George B. Oujevolk

[57] ABSTRACT

Oxyalkylene group of an alkylene oxide is inserted into a chain-type ether compound having at least one lower alkyl group by reacting the latter with the alkylene oxide in the presence of a catalyst prepared by mixing boron trifluoride and/or stannic chloride with an active-hydrogen compound exemplified by water or a lower aliphatic alcohol. The reaction results reduced formation of by-product dimer of the alkylene oxide even under an increased charging ratio of the alkylene oxide to the chain-type ether.

6 Claims, No Drawings

PROCESS FOR THE PRODUCTION OF ETHERS

CROSS-REFERENCE TO RELATED APPLICATION

This application is a continuation-in-part of U.S. application Ser. No. 161,930, filed on June 23, 1980, now abandoned.

BACKGROUND OF THE INVENTION

This invention relates to a process for the production of mono- or poly-glycol diethers and, more particularly, for the production of mono- or poly-glycol diethers by opening a ring of an alkylene oxide which is inserted into a chain-type ether compound having at least one lower alkyl group.

BRIEF DESCRIPTION OF THE PRIOR ART

Mono- or poly-glycol diethers have been long used as polor solvents having no active hydrogen in various fields. Various preparation methods, such as so-called indirect methods such as the Williamson process or his improved synthetic method, dialkyl sulfate method or hydrogenation of diglycol ether formal, have been industialized or proposed so far. A proposed production method a so-called direct method, is one where an alkylene oxide ring is opened and inserted into a chain-type ether in the presence of Lewis acids (Japanese Open Patent No. 53-34709, corresponds to U.S. Pat. No. 4,146,736 and German Open Patent No. 2640505). The present invention also relates to an alkylene oxide insertion reaction.

Few reports on the direct method of inserting the alkylene oxide into the chain-type ether have been published. Only a few examples are able to be cited, namely H. Meerwain "Journal für praktishe Chemie" N.F. Band 154, 83-153 (1939.), which refers to the preparation of γ-chloropropylene glycol diethyl ether from diethyl ether and epichlorohydrin, and butylene glycol diethyl ether from diethyl ether and butylene oxide, in the presence of boron trifluoride diethyl etherate or stannic chloride, and the Japanese Open Patent No. 53-34709 mentioned above.

Industrial advantages of the direct method are not only simplification of the production process but also to yield no by-products such as a large amount of sodium chloride and sodium sulfate in the indirect method or glycol monoethers in the formal hydrogenation. Therefore, it is an economically and efficiently surpassing method. However, an inevitable disadvantage in the direct methods with Lewis acid according to the Japanese Open Patent No. 53-34709, is that a large amount of alkylene oxide cyclic dimer is unavoidably formed as by-product reducing the yield of the objective, mono- or poly-glycol diether. This cyclic dimer is mainly formed by direct cyclization of two molecules of the alkylene oxide and its formation rate is chiefly dependent upon molar ratio of the alkylene oxide to the chain-type ether. Therefore, if it is intended to decrease the formation rate, a molar ratio of the alkylene oxide to the chain ether should be required to decrease as small as 0.02 to 0.5, which leads to inefficient and uneconomical results such as limited producibility, lowering of efficiency of instruments, or necessity of considerable amount of time and expense for recovering unreacted materials.

SUMMARY OF THE INVENTION

The inventors have investigated various preparation methods, using catalysts other than Lewis acids, to reduce disadvantages existing in the direct method with Lewis acids, and unexpectedly found that alkylene glycol diethers can be produced by a reaction of an alkylene oxide and a chain-type ether compound in the presence of a catalyst prepared by mixing boron trifluoride and/or stannic chloride with an active-hydrogen compound.

DESCRIPTION OF THE PREFERRED EMBODIMENTS

It is surprising that when the reaction is carried out using the above-mentioned catalyst, the selectivity of the alkylene oxide to the objective diether is improved to result in reduced formation of the by-product cyclic dimer even under an increased charging ratio of the alkylene oxide to the chain-type ether, and more uniform insertion of the alkylene oxide into the chain-type ether is achieved, in comparison with the direct method with Lewis acids.

In the invention, when an active-hydrogen compound details of which is described later is mixed, for example, with boron trifluoride, it is believed that formation of a complex ion occurs as shown hereunder, and the complex ion thus formed is effective as the catalyst to the advantage of the present invention.

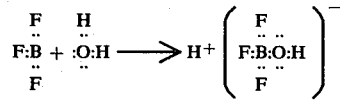

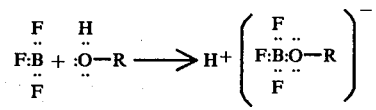

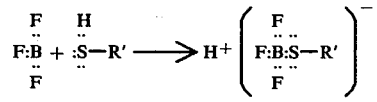

Since boron trifluoride or stannic chloride itself serves as a catalyst in the reaction of the present invention, when a too small amount of an active-hydrogen compound is mixed with boron trifluoride or stannic chloride, the amount of the complex ion catalyst formed by the mixture is too small to effect the invention. Accordingly, the amount of an active-hydrogen compound to be mixed with boron trifluoride or stannic chloride is 1 mole or above per mole of boron trifluoride or stannic chloride. However, if too much of an active-hydrogen compound is used for the preparation of the complex ion catalyst, an excessive active-hydrogen compound, beyond that employed for formation of the catalyst, causes decrease of activity of the catalyst. For this reason, molar ratio of an active-hydrogen compound to be mixed with boron trifluoride or stannic chloride is settled as described later.

Since the complex ion catalyst of the present invention can easily be obtained by simple mixing of specified amounts of both components, its preparation may be carried out in a reaction system for the diether production process, as described in detail later.

As the starting ether of the present invention, ether compounds having lower alkyl ether can be widely employed and, more particularly, those are represented by the general formula (1):

  (I)

wherein $R^1$ is a lower alkyl group, $R^2$ is an alkyl group having 1 to 12 carbon atoms, a phenyl group or a phenyl group substituted by lower alkyl or alkoxyl groups, or an aralkyl group formed by a lower alkylene and a phenyl group, m is an integer from 1 to 4, and n is a number from 0 to 8. When n is 2 or more, it is sometimes expressed as an average number of a mixture of various components.

The ether compound having a lower alkyl group according to this invention tends to have strong reactivity when $R^1$ and/or $R^2$ have lower carbon atom numbers and m and n are smaller. Particularly, either $R^1$ or $R^2$ is preferably a methyl or ethyl group, and compounds containing the methyl group are particularly effective in this invention. Examples of the particularly preferred lower alkyl ethers are as follows: dialkyl ethers such as dimethyl ether, diethyl ether, methyl ethyl ether, methyl propyl ether, methyl butyl ether, methyl pentyl ether, methyl hexyl ether, methyl decyl ether or methyl dodecyl ether; alkyl aralkyl ethers such as benzyl methyl ether or benzyl ethyl ether; dialkyl formals such as dimethyl formal, diethyl formal or methyl benzyl formal; alkylene glycol diethers such as ethylene glycol dimethyl ether, diethylene glycol dimethyl ether, ethylene glycol methyl ethyl ether, ethylene glycol diethyl ether, 1,3-propylene glycol dimethyl ether, 1,3-propylene glycol methyl ethyl ether, 1,4-butylene glycol dimethyl ether, ethylene glycol methyl phenyl ether or ethylene glycol methyl benzyl ether and mixtures thereof.

Various alkylene oxides may be used in this invention, particularly the prefered compounds are represented by the general formulas (II) or (III):

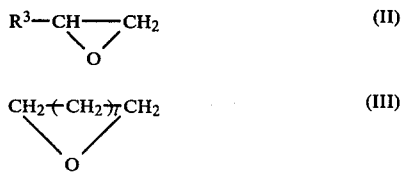

wherein $R^3$ represents a halogen-substituted or non-substituted alkyl group having between 1 and 5 carbon atoms or a phenyl group, and l is an integer from 0 to 5. The suitable examples are ethylene oxide, 1,2-propylene oxide, 1,2-butylene oxide, epichlorohydrin, styrene oxide, trimethylene oxide, tetramethylene oxide, pentamethylene oxide, hexamethylene oxide and mixtures thereof. Ethylene oxide and epichlorohydrin are particularly preferred.

As for boron trifluoride and stannic chloride in the present invention, boron trifluoride may be used by itself or in the form of an ether-complex whose ether may be the same or different from the starting chain-type ether of this invention. The stannic chloride can be employed either by itself or an ether complex. A mixture of boron trifluoride and stannic chloride may preferably be used.

As the active-hydrogen compound of this invention, the compounds having hydrogen bonding to a hetero atom such as an oxygen or sulfur atom are widely employable. Water, alcohols, carboxylic acids, phenols, sulfonic acids, mercaptans, hydroxamic acids and mixtures thereof are particularly preferred. The reaction is not hindered if some active hydrogens are bonded to various different hetero atoms in a molecule simultaneously. Suitable examples are as follows:

Alcohols: Aliphatic primary, secondary or, tertiary alcohols such as methanol, ethanol, primary, secondary or tertiary butanol, amylalcohol, octanol or higher alcohols and these having substituents such as aromatic groups, halogen atoms or alkoxyl groups; aliphatic polyhydric alcohols such as ethylene glycol, propylene glycol, 1,4-butanediol, 1,6-hexanediol, glycerol, pentaerythritol or polyvinyl alcohol and these polyhydric alcohols having substituents such as aromatic groups, halogen atoms or alkoxyl groups; and alicyclic alcohols such as substituted or non-substituted, cyclopentanol, cyclohexanol or cyclohexanediol.

Carboxylic acids: Substituted or non-substituted, straight-chain or cyclic, aliphatic or aromatic, mono- or poly-carboxylic acids and mixtures thereof. Suitable examples are aliphatic mono- or poly-carboxylic acids such as formic acid, acetic acid, propionic acid, butyric acid, hexane mono- or di-carboxylic acid, decane mono- or polycarboxylic acid, lauric acid, adipic acid, dodecane dicarboxylic acid, polyacrylic acid, polymethacrylic acid; aliphatic acids having substituents such as halogen atoms, alkoxyl, hydroxyl, aromatic or cycloalkyl groups, such as mono-, di- or tri-chloro acetic acids, methoxyacetic acid, lactic acid, oxypropionic acid, phenylacetic acid, cyclohexyl acetic acid; alicyclic mono- or polycarboxylic acids such as cyclobutane mono- or dicarboxylic acid, cyclohexane mono- or dicarboxylic acid, cyclooctane mono- or dicarboxylic acid and these alicyclic carboxylic acids having substituents such as halogen atoms, alkyl, aromatic or hydroxyl groups; aromatic carboxylic acids such as benzoic acid, tere-, ortho- or iso-phthalic acid, naphthalene carboxylic acid and these aromatic carboxylic acids having substituents such as halogen atoms, alkyl, hydroxyl, alkoxyl or aromatic groups, such as toluic acid, dimethyl benzoic acid, salicylic acid, para-oxybenzoic acid, ortho-methoxybenzoic acid, ortho-chlorobenzoic acid or 2-phenylbenzoic acid; or carboxylic acid-type ion exchange resins.

Phenols: Phenol, hydroquinone, catechol, resorcinol, naphthol, their derivatives substituted by halogen atoms, alkyl or alkoxyl groups and mixtures thereof.

Sulfonic acids: Aliphatic mono- or polysulfonic acids such as methane sulfonic acid, ethane sulfonic acid, propane sulfonic acid, ethane disulfonic acid or propane disulfonic acid; aliphatic sulfonic acids substituted by hydroxyl or carboxyl groups such as isethionic acid or sulfoacetic acid; aromatic mono- or polysulfonic acids such as benzene sulfonic acid, toluene sulfonic acid, xylene sulfonic acid, benzene disulfonic acid or naphthalene sulfonic acid; aromatic sulfonic acids substituted by halogen atoms, hydroxyl or alkoxyl groups such as 2-oxybenzene sulfonic acid, 2-methoxybenzene sulfonic acid or 2-chlorobenzene sulfonic acid; or sulfonic acid-type ion exchange resins.

Mercaptans: aliphatic or aralkyl mercaptans such as methylmercaptan, ethylmercaptan, butylmercaptan, amylmercaptan, hexylmercaptan, heptylmercaptan, octylmercaptan, nonylmercaptan, decylmercaptan, dodecylmercaptan, ethanedithiol, propanedithiol, butanedithiol and benzylmercaptan; hydroxy, halogen or carboxyl group substituted mercaptans such as monothioethyleneglycol, monothiopropyleneglycol, α-monothioglycerol, 1,2- or 1,3-dithioglycerol, monothioethylenechlorohydrin, 3-chloro-propylmercaptans, thioglycolic acid, thiolactic acid.

Hydroxamic acids: Acetohydroxamic acid, propio hydroxamic acid, laurohydroxamic acid, myristohydroxamic acid, stearohydroxamic acid and substituted derivatives thereof.

Although boron trifluoride or stannic chloride in this invention is not prevented from combination with a wide variety of the active-hydrogen compounds, each has the most suitable kinds and amounts of the active-hydrogen compounds. For boron trifluoride, for example, water, alcohols, carboxylic acids, phenols, sulfonic acids, mercaptans, and hydroxamic acids are mentioned. Stannic chloride prefers e.g. water, alcohols, phenols, carboxylic acids, and sulfonic acids.

Showing on the basis of numbers of active hydrogens per mole of boron trifluoride or stannic chloride, a suitable quantitative relation between boron trifluoride and water is 1 to 5, most preferably 1 to 3, between boron trifluoride and the active-hydrogen compounds other than water is 1 to 5 most preferably 1 to 2, and between stannic chloride and the active-hydrogen compounds is 1 to 5, most preferably 1 to 2.

It is unnecessary to distinguish multiple active-hydrogens among mixed active-hydrogen compounds and derived active hydrogens from various functional groups in a molecule. The active-hydrogen compounds described in the specification are illustrative only, and one skilled in the art will be able to use various alternatives based on the present specification.

However it is sometimes better to adopt a specific active-hydrogen compound on expecting other effects than control of alkylene oxide cyclic dimers, such as an increase of a poly glycol diether fraction in the system of boron trifluoride and water, or of a lower molecule glycol diether fraction in the system of stannic chloride and carboxylic acid and sulfonic acid.

As to the preparation of the catalyst, it can be made up by mixing specified amounts of boron trifluoride or stannic chloride with the active-hydrogen compound independently from the reaction system or in the reaction system prior to the reaction. For practical operations, catalysts prepared freshly in the reaction system are preferably employed for the successively commenced diether production reaction.

Reaction solvents may be employed if they have any advantages for preparation of catalysts and removal of a heat of reaction. Their examples are inactive solvents such as dichloromethane, nitromethane, chlorobenzene, benzene, acetic acid esters or reaction products themselves such as mono- or polyglycol diethers and the mixtures.

A continuous or batch process may be applied to the reaction, which can be carried out at under or atmospheric pressure depending on the vapour pressure of the starting ether and the alkylene oxide.

The reaction is preferably carried out under inert gas atmosphere such as nitrogen or helium gas in order to maintain catalyst activity, provide safe operation and to prevent side reactions.

The reaction temperature may be from 0° to 100° C., preferably 20° to 80° C.

The reaction rate is dependent on the concentration of the catalysts, on the reaction temperature, and on the kinds of the starting ethers and alkylene oxides. To gain a desired result, levels of the factors can be properly selected.

The preferred amount of boron trifluoride and/or stannic chloride is 0.01 to 10 mole percent, more particularly 0.05 to 5 mole percent, relative to the starting ether.

The composition of the end product can be regulated by adjusting the molar ratio of the starting ether and the alkylene oxide. In other words, the product is a mixture of alkylene glycol diethers having a wide molecular distribution of oxyalkylene groups. If it is intended to obtain a mixture of homologs of an average lower chain length, the ratio of the alkylene oxide to the starting ether is decreased; this ratio can be increased for obtaining a mixture of homologs of a higher chain length. If the ratio of the alkylene oxide to ether is extremely large, the effect of repressing the alkylene oxide dimers will be decreased, so that the molar ratio of the alkylene oxide to the starting ether is preferably of 0.5 to 10, more particularly, 0.5 to 5. The larger expansion of the upperlimit value of the range in the present invention, as compared with that of single-Lewis acid catalyst process, improves the efficiency and the economics of the process on an industrial scale.

Although each starting material and catalyst according to the present invention can be charged simultaneously into the reaction, it is advantageous that the alkylene oxide or the alkylene oxide and the starting ether are gradually added to the reaction solvent in which the catalyst is dissolved, in order to control a heat of reaction.

In general, the reaction products are thus obtained, and after deactivation and removal of the catalysts by inorganic or organic base compounds or ion exchange resins, may furthermore, if desired, be purified by eliminating traces of impurities by using activated carbon adsorption or by alkylating traces of hydroxyl groups by using alkylating agents such as dialkyl sulfate or halogenated hydrocarbons, after which the reaction mixture can be purified by distillation.

The unreacted starting ether is recovered by atmospheric or pressure distillation and then, the objective alkylene glycol diether, with a single component or a mixture of homologs can be distilled under at atmospheric or reduced pressure. The mixture of the polyglycol diethers can preferably be purified by thin-film evaporation or merely by salting out and separating the products with an alkali washing, whose organic layer itself can be offered as a commercial product. Although, during the distillation, it is advisable to neutralize or remove the acid from the reaction mixture e.g. the catalyst, for prevention of decomposition of the product, it may be possible to recover by distillation at a low temperature the boron trifluoride complex, especially its etherate.

The present invention is explained in the following examples:

EXAMPLE 1

Initially, into a 500 ml autoclave sufficiently flushed with nitrogen, were charged 0.004 moles (0.5 g) of boron trifluoride dimethyl ether complex and 0.004 moles (0.08 g) of water, and the charged materials were dissolved in 40 g of dichloromethane to prepare the catalyst solution. To the solution, was added 1 mole (46 g) of dimethyl ether under cooling, and then 1 mole (44 g) of ethylene oxide was introduced gradually at 40° C. under stirring, and the reaction was continued for 10 minutes.

After completion of the reaction, the reaction mixture was cooled to room temperature without delay and unreacted dimethyl ether was recovered by condensing with dry ice-methanol. The residual product was analysed by gas chromatography to give the result shown in Table 1.

After the completion of the reaction, the reaction mixture was treated as Example 1 to give the result shown in Table 3.

EXAMPLE 3

Example 2 was repeated except that total dimethyl ether was 1 mole (46 g) and 3 moles (132 g) of ethylene oxide was introduced at 55° C. in the course of 2.5 hours. The result is shown in Table 3.

TABLE 1

| Conversion (%) | | | Selectivity (based on ethylene oxide) (%) | | | | | | | | | |
|---|---|---|---|---|---|---|---|---|---|---|---|---|
| | $\overset{CH_2-CH_2}{\underset{O}{\diagdown\diagup}}$ | | $CH_3O-(CH_2CH_2O)_n-CH_3$ | | | | | | | | | (*) |
| $CH_3OCH_3$ | | n = 1 | 2 | 3 | 4 | 5 | 6 | 7 | Total | 1,4-Dioxane | Others |
| 38.4 | 99.5 | 16.6 | 18.4 | 15.6 | 13.0 | 10.0 | 7.1 | 4.5 | 85.2 | 12.9 | 2.0 |

(*) Others are acetoaldehyde, mono- and polyethylene glycol monomethyl ethers and polyethylene glycols.

COMPARISON EXAMPLE 1

Example 1 was repeated without addition of water for preparation of the catalyst. The result is shown in Table 2.

EXAMPLE 4

Example 3 was repeated except that 5 moles (220 g) of ethylene oxide was introduced at 55° C. in the course of 3.5 hours. The result is shown in Table 3.

TABLE 3

| | Raw materials amounts charged (moles) | | | | | Selectivity (%) *1 | | |
|---|---|---|---|---|---|---|---|---|
| Example No. | $CH_3OCH_3$ (A) | $\overset{CH_2-CH_2}{\underset{O}{\diagdown\diagup}}$ (B) | molar ratio B/A | Conversion (%) A | B | Glycol *2 dimethyl ethers | 1,4-Dioxane | Others |
| 2 | 5 | 1 | 1/5 | 15.8 | 99.1 | 96.5 | 2.5 | 0.3 |
| 3 | 1 | 3 | 3/1 | 75.6 | 99.0 | 62.5 | 36.1 | 1.4 |
| 4 | 1 | 5 | 5/1 | 85.2 | 98.6 | 46.8 | 51.2 | 2.0 |

*1 Based on ethylene oxide
*2 Mixture of mono- and poly-glycol dimethyl ether.

TABLE 2

| Conversion (%) | | | Selectivity (based on ethylene oxide) (%) | | | | | | | | | |
|---|---|---|---|---|---|---|---|---|---|---|---|---|
| | $\overset{CH_2-CH_2}{\underset{O}{\diagdown\diagup}}$ | | $CH_3O-(CH_2CH_2O)_n-CH_3$ | | | | | | | | | (*) |
| $CH_3OCH_3$ | | n = 1 | 2 | 3 | 4 | 5 | 6 | 7 | Total | 1,4-Dioxane | Others |
| 41.4 | 99.4 | 26.8 | 17.1 | 10.8 | 6.5 | 2.9 | 1.7 | 0.7 | 66.5 | 33.1 | 0.3 |

(*) Others are same with Table 1.

EXAMPLE 2

Initially, into a 500 ml autoclave sufficiently flushed with nitrogen, were charged 46 g (1.0 mole) of dimethyl ether, 0.004 moles (0.5 g) of boron trifluoride dimethyl ether complex and 0.004 moles (0.08 g) of water, and the charged materials were stirred. To this solution, 4.0 moles (184 g) of dimethyl ether was added further, and then 1 mole (44 g) of ethylene oxide was introduced at 55° C. in the course of one hour, and stirring at 55° C. was continued for further half an hour.

COMPARISON EXAMPLES 2-4

Examples 2, 3 and 4 were repeated without addition of water. The results are shown in Table 4.

TABLE 4

| | Raw materials amounts charged (moles) | | | | | Selectivity (%) *1 | | |
|---|---|---|---|---|---|---|---|---|
| Comparison Example No. | $CH_3OCH_3$ (A) | $\overset{CH_2-CH_2}{\underset{O}{\diagdown\diagup}}$ (B) | molar ratio B/A | Conversion (%) A | B | Glycol *2 dimethyl ethers | 1,4-Dioxane | Others |
| 2 | 5 | 1 | 1/5 | 16.2 | 99.5 | 90.4 | 7.48 | 0.4 |
| 3 | 1 | 3 | 3/1 | 71.0 | 98.8 | 50.9 | 48.9 | 0.2 |
| 4 | 1 | 5 | 5/1 | 82.8 | 98.6 | 42.0 | 57.9 | 0.1 |

*1 and *2 are same with Table 3.

EXAMPLES 5 AND 6

Example 1 was repeated with the following varied amounts of water for preparation of the catalyst. The results are shown in Table 6.

| Example No. | Amount of water added |
|---|---|
| 5 | 0.17 g (2.1)* |
| 6 | 0.37 g (4.7) |

( ) represents molar ratio of $H_2O/BF_3$ dimethyl ether complex.

TABLE 6

| Example No. | Conversion (%) A | B | Selectivity (based on ethylene oxide) (%) $CH_3O—(CH_2CH_2O)_n—CH_3$ | | | | | | | | | C | D |
|---|---|---|---|---|---|---|---|---|---|---|---|---|---|
| | | | n = 1 | 2 | 3 | 4 | 5 | 6 | 7 | 8 | Total | | |
| 5 | 33.2 | 99.4 | 11.3 | 16.2 | 14.7 | 13.5 | 9.9 | 7.9 | 5.9 | 4.6 | 84.0 | 12.5 | 3.3 |
| 6 | 35.2 | 99.5 | 13.2 | 17.2 | 14.9 | 12.4 | 9.3 | 5.4 | 4.1 | 0.7 | 77.6 | 12.0 | 10.3 |

A: dimethyl ether;
B: ethylene oxide;
C: 1,4-dioxane;
D: others which are same with Table 1.

the catalyst solution. To the solution, was added 1 mole (46 g) of dimethyl ether under cooling, and then 1 mole (44 g) of ethylene oxide was introduced at 50° C., and the reaction was continued for 1 hour under stirring.

After the reaction was completed, the reaction mixture was treated as Example 1 to give results shown in Table 7.

TABLE 7

| Conversion (%) A | B | Selectivity (based on ethylene oxide) (%) $CH_3O—(CH_2CH_2O)_n—CH_3$ | | | | | | | | | | C | D |
|---|---|---|---|---|---|---|---|---|---|---|---|---|---|
| | | n = 1 | 2 | 3 | 4 | 5 | 6 | 7 | 8 | 9 | Total | | |
| 48.0 | 99.3 | 29.3 | 20.6 | 13.1 | 8.1 | 4.4 | 2.3 | 1.2 | 0.6 | 0.2 | 79.8 | 16.8 | 3.4 |

A: dimethyl ether;
B: ethylene oxide;
C: 1,4-dioxane;
D: others which are same with Table 1.

EXAMPLE 7

Into a 500 ml autoclave sufficiently flushed with nitrogen, were charged 0.002 moles (0.25 g) of boron trifluoride dimethyl ether complex and 0.002 moles (0.07 g) of methyl alcohol, and the charged materials were dissolved in 40 g of dichloromethane to prepare

EXAMPLES 8–40

Example 7 was repeated except that 1:1 molar ratio of respective active-hydrogen compounds to boron trifluoride on the basis of number of active-hydrogen was added. The results obtained are shown in Table 8.

TABLE 8

| Example No. | Organic active-hydrogen compound | Conversion (%) $CH_3OCH_3$ | $CH_2$—$CH_2$ \\ O / | 1,4-Dioxane | (*1) Others | Selectivity (based on ethylene oxide) (%) $CH_3—O(CH_2CH_2O)_{\overline{n}}CH_3$ | | | | | | | | | Total |
|---|---|---|---|---|---|---|---|---|---|---|---|---|---|---|---|
| | | | | | | n = 1 | 2 | 3 | 4 | 5 | 6 | 7 | 8 | 9 | |
| 8 | Amyl alcohol | 52.5 | 99.4 | 14.5 | 2.1 | 34.3 | 21.7 | 12.7 | 7.4 | 3.9 | 2.0 | 0.8 | 0.4 | 0.2 | 83.4 |
| 9 | Nonyl alcohol | 50.5 | 99.1 | 15.9 | 4.0 | 32.6 | 20.7 | 12.2 | 7.5 | 3.8 | 1.8 | 0.9 | 0.5 | 0.1 | 80.1 |
| 10 | Stearyl alcohol | 50.1 | 99.1 | 17.1 | 3.1 | 32.9 | 20.0 | 12.5 | 7.4 | 4.0 | 1.5 | 0.9 | 0.5 | 0.1 | 79.8 |
| 11 | sec.-Butanol | 49.4 | 99.3 | 16.4 | 2.5 | 31.1 | 20.8 | 12.8 | 8.0 | 4.6 | 2.2 | 1.0 | 0.5 | 0.1 | 81.1 |
| 12 | tert.-Butanol | 48.4 | 99.0 | 15.0 | 4.1 | 29.6 | 22.0 | 13.1 | 7.9 | 4.2 | 2.1 | 1.2 | 0.6 | 0.2 | 80.9 |
| 13 | Benzyl alcohol | 51.0 | 99.2 | 14.8 | 3.5 | 33.3 | 20.8 | 12.6 | 7.4 | 4.1 | 2.1 | 0.9 | 0.4 | 0.1 | 81.7 |
| 14 | Ethylene glycol monomethyl ether | 51.3 | 99.4 | 15.1 | 3.0 | 33.4 | 21.3 | 12.5 | 7.3 | 4.1 | 2.1 | 0.8 | 0.3 | 0.1 | 81.9 |
| 15 | Cyclohexane diol | 47.8 | 99.1 | 17.8 | 2.0 | 30.0 | 19.7 | 12.8 | 8.2 | 4.8 | 2.5 | 1.3 | 0.7 | 0.2 | 80.2 |
| 16 | Ethylene glycol | 49.9 | 99.3 | 15.5 | 5.1 | 32.5 | 20.6 | 12.1 | 7.0 | 3.9 | 1.9 | 1.0 | 0.3 | 0.1 | 79.4 |
| 17 | Glycerol | 48.9 | 99.1 | 16.4 | 3.3 | 31.4 | 20.1 | 12.3 | 7.6 | 5.2 | 2.0 | 1.0 | 0.5 | 0.1 | 80.3 |
| 18 | Pentaerythritol | 50.3 | 99.3 | 16.0 | 3.5 | 32.9 | 20.2 | 12.5 | 8.0 | 3.7 | 1.8 | 0.8 | 0.5 | 0.1 | 80.5 |
| 19 | Polyvinyl alcohol (molecular weight 2000) | 49.1 | 99.0 | 18.4 | 4.0 | 32.9 | 19.4 | 11.5 | 7.0 | 3.5 | 1.9 | 0.8 | 0.5 | 0.1 | 77.6 |
| 20 | Formic acid | 47.3 | 99.5 | 16.1 | 2.9 | 28.7 | 20.4 | 13.0 | 8.9 | 5.1 | 2.6 | 1.4 | 0.7 | 0.3 | 81.0 |
| 21 | Acetic acid | 49.7 | 99.3 | 16.9 | 2.7 | 32.1 | 20.1 | 12.4 | 7.9 | 4.5 | 2.0 | 0.8 | 0.5 | 0.1 | 80.4 |
| 22 | Lactic acid | 50.7 | 99.3 | 17.2 | 2.5 | 33.2 | 20.9 | 12.2 | 7.0 | 3.7 | 1.9 | 0.9 | 0.4 | 0.1 | 80.3 |
| 23 | Lauric acid | 49.6 | 99.1 | 16.8 | 3.5 | 32.3 | 20.4 | 12.2 | 7.4 | 4.0 | 1.9 | 0.9 | 0.5 | 0.1 | 79.7 |
| 24 | Monochloro acetic acid | 49.0 | 99.2 | 16.9 | 2.4 | 30.8 | 20.8 | 13.1 | 8.1 | 4.6 | 2.0 | 0.8 | 0.4 | 0.1 | 80.7 |
| 25 | Phenyl acetic acid | 48.6 | 99.0 | 17.0 | 3.0 | 32.0 | 20.0 | 12.7 | 7.7 | 4.4 | 1.9 | 0.8 | 0.4 | 0.1 | 80.0 |
| 26 | Benzoic acid | 49.0 | 99.0 | 13.3 | 3.4 | 31.7 | 20.2 | 12.4 | 7.5 | 4.0 | 2.0 | 1.0 | 0.4 | 0.1 | 79.3 |
| 27 | Terephthalic acid | 48.0 | 99.1 | 17.5 | 2.9 | 31.1 | 20.3 | 12.6 | 7.7 | 4.4 | 2.1 | 0.8 | 0.4 | 0.1 | 79.6 |
| 28 | Naphthalene carboxylic acid | 47.2 | 99.0 | 20.2 | 3.4 | 30.4 | 19.9 | 11.7 | 7.4 | 3.8 | 1.8 | 0.8 | 0.4 | 0.2 | 76.4 |
| 29 | Adipic acid | 48.4 | 99.3 | 17.5 | 3.5 | 30.9 | 20.0 | 12.6 | 7.6 | 4.1 | 2.2 | 1.0 | 0.5 | 0.1 | 79.0 |
| 30 | Polyacrylic acid (molecular weight 2000) | 48.9 | 99.3 | 17.6 | 3.3 | 31.1 | 20.6 | 12.5 | 7.7 | 3.9 | 2.0 | 0.8 | 0.4 | 0.1 | 79.1 |
| 31 | Carboxylic acid-type (*2) ion exchange resin | 48.1 | 99.2 | 18.9 | 3.6 | 30.8 | 20.0 | 12.2 | 7.7 | 3.8 | 1.7 | 0.8 | 0.3 | 0.1 | 77.5 |
| 32 | Methane sulfonic acid | 46.5 | 99.5 | 13.8 | 3.7 | 26.8 | 21.0 | 13.9 | 9.2 | 5.5 | 3.1 | 1.7 | 0.9 | 0.4 | 82.5 |
| 33 | 1,2-Ethane disulfonic acid | 46.0 | 99.5 | 14.1 | 3.9 | 26.2 | 21.5 | 13.4 | 9.7 | 5.4 | 2.9 | 1.7 | 0.9 | 0.3 | 82.0 |
| 34 | Benzen sulfonic acid | 46.3 | 99.4 | 15.5 | 2.1 | 26.8 | 21.1 | 13.7 | 9.3 | 5.5 | 3.5 | 1.6 | 0.7 | 0.2 | 82.4 |
| 35 | p-Toluene sulfonic acid | 45.8 | 99.4 | 15.9 | 2.4 | 26.3 | 20.9 | 13.7 | 9.0 | 5.3 | 3.4 | 1.8 | 0.9 | 0.4 | 81.7 |

TABLE 8-continued

| Example No. | Organic active-hydrogen compound | Conversion (%) | | | | Selectivity (based on ethylene oxide) (%) | | | | | | | | | |
|---|---|---|---|---|---|---|---|---|---|---|---|---|---|---|---|
| | | CH$_3$OCH$_3$ | CH$_2$—CH$_2$ \\O/ | 1,4-Dioxane | (*1) Others | CH$_3$—O$\leftarrow$CH$_2$CH$_2$O$\rightarrow_n$CH$_3$ | | | | | | | | | Total |
| | | | | | | n = 1 | 2 | 3 | 4 | 5 | 6 | 7 | 8 | 9 | |
| 36 | Sulfonic acid-type (*3) ion exchange resin | 46.4 | 99.3 | 18.1 | 4.2 | 28.7 | 19.7 | 12.5 | 7.5 | 4.5 | 2.7 | 1.4 | 0.5 | 0.2 | 77.7 |
| 37 | Phenol | 46.2 | 99.0 | 21.5 | 4.0 | 29.9 | 18.8 | 11.8 | 7.0 | 3.9 | 1.8 | 0.8 | 0.4 | 0.1 | 74.5 |
| 38 | Hydroquinone | 46.2 | 99.1 | 21.1 | 4.1 | 29.6 | 19.1 | 11.8 | 7.4 | 3.7 | 2.0 | 0.8 | 0.3 | 0.1 | 74.8 |
| 39 | Ethyl mercaptan | 47.1 | 99.2 | 20.5 | 3.8 | 30.5 | 19.2 | 11.4 | 7.4 | 4.1 | 1.8 | 0.8 | 0.4 | 0.1 | 75.7 |
| 40 | Aceto hydroxamic acid | 46.9 | 98.8 | 15.8 | 3.0 | 28.4 | 20.1 | 14.4 | 8.3 | 4.9 | 2.6 | 1.4 | 0.8 | 0.3 | 81.2 |

(*1) others which are same with Table 1
(*2) DAIYA ION WK-20 (Trademark of Mitsubishi Kasei Co., Ltd.)
(*3) DAIYA ION PK-228 (Trademark of Mitsubishi Kasei Co., Ltd.)

EXAMPLE 41

Example 8 was repeated except that the molar ratio of amyl alcohol/BF$_3$ was 2/1. The result is shown in Table 9.

TABLE 9

| Conversion (%) | | Selectivity (based on ethylene oxide) (%) | | | | | | | | | | |
|---|---|---|---|---|---|---|---|---|---|---|---|---|
| A | B | CH$_3$O—(CH$_2$CH$_2$O)$_n$—CH$_3$ | | | | | | | | | C | D |
| | | n = 1 | 2 | 3 | 4 | 5 | 6 | 7 | 8 | 9 | Total | |
| 50.3 | 99.4 | 32.9 | 20.9 | 12.2 | 7.5 | 3.8 | 1.8 | 0.9 | 0.5 | 0.2 | 80.7 | 15.0 4.3 |

A: dimethyl ether;
B: ethylene oxide;
C: 1,4-dioxane;
D: others which are same with Table 1.

EXAMPLE 42

Into the equipment same as mentioned in Example 1 were charged 80 g of methylal and 1 mole % of water based on methylal.* To the charged materials were introduced 1 mole % of gaseous boron trifluoride based on methylal and 9.2 g of ethylene oxide, and the reaction was conducted for 10 minutes at 40° C., for 20 minutes at 60° C. and for 20 minutes at 80° C. The result is shown in Table 10.
*CH$_3$OCH$_2$OCH$_3$

EXAMPLE 43

Example 42 was repeated except that 0.5 mole % of p-toluene sulfonic acid based on methylal as the active-hydrogen compound and 0.5 mole % of gaseous boron trifluoride were charged, and the reaction was conducted at 80° C. for 2 hours. The result is shown in Table 10.

COMPARISON EXAMPLES 5 AND 6

Examples 42 and 43 were repeated without adding any active-hydrogen compound. The results are shown in Table 10.

TABLE 10

| Example & Comparison Example | Conversion (%) | | Selectivity (based on ethylene oxide) (%) | | | | | | |
|---|---|---|---|---|---|---|---|---|---|
| | methylal | ethylene oxide | RO—(CH$_2$CH$_2$O)$_n$—R$^1$ (*) | | | | | | 1,4-Dioxane |
| | | | n = 1 | 2 | 3 | 4 or more | Total | | |
| Example 42 | 9.6 | 99.0 | 24.3 | 25.2 | 23.4 | 11.7 | 84.7 | | 5.2 |
| Comp. Ex. 5 | 13.9 | 99.3 | 58.1 | 15.3 | 8.2 | 3.0 | 84.6 | | 12.2 |
| Example 43 | 14.1 | 99.1 | 61.0 | 15.4 | 9.3 | 3.7 | 89.4 | | 7.1 |
| Comp. Ex. 6 | 13.4 | 99.3 | 58.0 | 14.9 | 8.1 | 3.0 | 84.0 | | 12.8 |

(*) The product is a mixture having molecular structures of which ethylene oxide which was inserted in a side of the oxymethylene group or both sides, but the expression ignores the order of $-(CH_2O)-$ and $-(CH_2CH_2O)-$.

EXAMPLE 44 AND COMPARISON EXAMPLE 7

Into a 500 ml four necked flask equipped with a stirrer, a condenser, a thermometer and a dropping funnel, were charged 1 mole (90 g) of ethylene glycol dimethyl ether, 0.03 moles (3.4 g) of boron trifluoride dimethyl ether complex and 0.03 moles (0.9 g) of methanol for Example 44 but without adding methanol for Comparison Example 7. To the charged materials, 0.5 moles (46.3 g) of epichlorohydrin was dropped under stirring in the course of 2 hours at 50° C. The results are shown in Table 11.

TABLE 11

| Example & Comparison Example | Conversion (%) | | Selectivity (based on epichlorohydrin) (%) | | | | | |
|---|---|---|---|---|---|---|---|---|
| | A | B | CH$_3$O—(CH$_2$CH$_2$O)—(CHCH$_2$O)$_n$—CH$_3$ (%) (*)<br>$\quad\quad\quad\quad\quad\quad\quad\quad\quad\quad\quad\quad\quad\quad$ \|<br>$\quad\quad\quad\quad\quad\quad\quad\quad\quad\quad\quad\quad\quad\quad$ CH$_2$Cl | | | | | C |
| | | | n = 1 | 2 | 3 | 4 or more | Total | |
| Example 44 | 37.9 | 98.1 | 65.2 | 18.2 | 6.0 | 0.9 | 90.1 | 5.3 |
| Comp. Ex. 7 | 27.5 | 97.9 | 69.4 | 14.5 | 3.9 | 0.0 | 87.8 | 8.2 |

A: ethylene glycol dimethyl ether;
B: epichlorohydrin;
C: 2,5-dichloromethyl-1,4-dioxane (*) The expression ignores the order of $-(CH_2CH_2O)-$ and $-(CHCH_2O)-$.
$\quad\quad\quad\quad\quad\quad\quad\quad\quad\quad\quad\quad\quad\quad\quad\quad\quad$ |
$\quad\quad\quad\quad\quad\quad\quad\quad\quad\quad\quad\quad\quad\quad\quad\quad\quad$ CH$_2$Cl

EXAMPLE 45

Into an autoclave, were charged 0.0025 moles (0.6 g) of anhydrous stannic chloride and 0.0025 moles (0.15 g) of acetic acid, and the charged materials were dissolved in 20 g of dichloromethane to prepare the catalyst solution. To the solution, were added 0.5 moles (23 g) of dimethyl ether and 0.5 moles (22 g) of ethylene oxide, and the mixture was shaken at 25° to 50° C. for an hour. After the reaction had done, the reaction mixture was treated as Example 1. The result is shown in Table 12.

TABLE 12

| Conversion (%) | | Selectivity (based on ethylene oxide) (%) | | | | | | | | | | | |
|---|---|---|---|---|---|---|---|---|---|---|---|---|---|
| | | $CH_3O-(CH_2CH_2O)_n-CH_3$ | | | | | | | | | | | |
| A | B | n = 1 | 2 | 3 | 4 | 5 | 6 | 7 | 8 | 9 | Total | C | D |
| 48.7 | 99.4 | 29.7 | 19.2 | 12.2 | 7.7 | 4.5 | 2.7 | 1.5 | 0.9 | 0.5 | 78.9 | 15.0 | 6.1 |

A: dimethyl ether;
B: ethylene oxide;
C: 1,4-dioxane;
D: other which are same with Table 1.

COMPARISON EXAMPLE 8

Example 45 was repeated except adding acetic acid. The results are shown in Table 13.

TABLE 13

| Conversion (%) | | Selectivity (based on ethylene oxide) (%) | | | | | | | | | | | |
|---|---|---|---|---|---|---|---|---|---|---|---|---|---|
| | | $CH_3O-(CH_2CH_2O)_n-CH_3$ | | | | | | | | | | | |
| A | B | n = 1 | 2 | 3 | 4 | 5 | 6 | 7 | 8 | 9 | 10 | Total | C | D |
| 33.1 | 99.3 | 17.7 | 11.6 | 8.6 | 6.7 | 5.7 | 4.5 | 3.8 | 3.1 | 2.6 | 2.0 | 66.3 | 26.8 | 6.9 |

A: dimethyl ether;
B: ethylene oxide;
C: 1,4-dioxane
D: others which are same with Table 1.

EXAMPLES 46–63

Example 45 was repeated except that 1:1 molar ratio of respective carboxylic or sulfonic acid to stannic chloride on the basis of the number of active-hydrogen was added. The results are shown in Table 14.

TABLE 14

| Example No. | Carboxylic acid or sulfonic acid | Conversion (%) | | Selectivity (based on ethylene oxide) (%) | | | | | | | | | | | |
|---|---|---|---|---|---|---|---|---|---|---|---|---|---|---|---|
| | | | | $CH_3O+(CH_2CH_2O)_n CH_3$ Composition (%) | | | | | | | | | | | |
| | | A | B | n = 1 | 2 | 3 | 4 | 5 | 6 | 7 | 8 | 9 | Total | C | D |
| 46 | Formic acid | 49.6 | 99.2 | 30.3 | 19.8 | 12.4 | 7.8 | 4.5 | 2.6 | 1.5 | 0.9 | 0.4 | 80.2 | 13.8 | 6.0 |
| 47 | Butyric acid | 48.1 | 99.1 | 29.2 | 19.3 | 12.3 | 7.7 | 4.5 | 2.4 | 1.4 | 0.8 | 0.2 | 77.8 | 16.0 | 6.2 |
| 48 | Lauric aicd | 46.2 | 99.2 | 27.2 | 18.3 | 12.4 | 7.8 | 5.2 | 3.3 | 2.0 | 1.4 | 0.6 | 78.2 | 15.5 | 6.3 |
| 49 | Adipic acid | 49.8 | 99.3 | 30.7 | 19.9 | 13.1 | 6.6 | 4.2 | 2.4 | 1.3 | 0.6 | 0.3 | 79.1 | 14.0 | 6.9 |
| 50 | Lactic acid | 49.3 | 99.5 | 29.8 | 19.5 | 13.4 | 6.9 | 4.8 | 2.9 | 1.7 | 0.8 | 0.4 | 80.2 | 12.8 | 7.0 |
| 51 | Monochloro acetic acid | 49.4 | 99.1 | 30.1 | 19.7 | 12.5 | 7.9 | 4.8 | 2.6 | 1.5 | 0.9 | 0.3 | 80.3 | 13.4 | 6.3 |
| 52 | Phenyl acetic acid | 47.6 | 99.4 | 28.8 | 19.0 | 12.2 | 7.6 | 4.4 | 2.4 | 1.5 | 0.6 | 0.2 | 76.7 | 17.8 | 5.5 |
| 53 | Polyacrylic acid (molecular weight 2000) | 47.8 | 99.5 | 29.0 | 18.9 | 12.2 | 7.6 | 4.3 | 2.4 | 1.3 | 0.6 | 0.3 | 76.6 | 16.5 | 6.9 |
| 54 | Cyclohexane carboxylic acid | 47.6 | 99.1 | 28.5 | 19.5 | 12.2 | 7.8 | 4.7 | 2.6 | 1.5 | 0.8 | 0.4 | 78.0 | 16.1 | 5.9 |
| 55 | Benzoic acid | 46.5 | 99.3 | 28.2 | 18.2 | 12.4 | 7.0 | 4.4 | 2.6 | 1.5 | 0.8 | 0.3 | 75.4 | 17.8 | 6.8 |
| 56 | Terephthalic acid | 48.0 | 99.2 | 29.5 | 18.9 | 12.7 | 6.8 | 4.2 | 2.3 | 1.5 | 0.6 | 0.3 | 76.8 | 17.0 | 6.2 |
| 57 | p-Oxybenzoic acid | 47.9 | 99.4 | 28.6 | 19.5 | 12.2 | 7.9 | 4.8 | 2.6 | 1.5 | 0.8 | 0.4 | 78.3 | 14.8 | 6.9 |
| 58 | Carboxylic acid-type (*1) ion exchange resin | 47.3 | 99.3 | 28.3 | 18.9 | 12.2 | 8.1 | 4.6 | 2.6 | 1.6 | 0.9 | 0.5 | 77.7 | 15.2 | 7.1 |
| 59 | Methane sulfonic acid | 44.3 | 99.4 | 25.4 | 17.6 | 12.1 | 8.0 | 4.8 | 3.8 | 3.0 | 1.6 | 0.7 | 77.0 | 15.9 | 7.1 |
| 60 | 1,2-Ethane disulfonic acid | 44.4 | 99.4 | 25.5 | 17.5 | 12.3 | 8.0 | 4.8 | 4.0 | 3.1 | 1.5 | 0.7 | 77.4 | 15.6 | 7.0 |
| 61 | p-Toluene sulfonic acid | 44.4 | 99.2 | 25.5 | 17.7 | 12.1 | 8.1 | 4.9 | 3.9 | 3.0 | 1.5 | 0.8 | 77.5 | 16.0 | 6.5 |
| 62 | 5-Sulfo salicylic acid | 47.3 | 99.3 | 27.9 | 18.6 | 13.1 | 7.5 | 5.0 | 3.5 | 2.3 | 1.4 | 0.8 | 80.1 | 13.0 | 6.9 |
| 63 | Sulfonic acid-type (*2) ion exchange resin | 46.6 | 99.3 | 27.5 | 18.9 | 12.2 | 8.3 | 4.8 | 2.9 | 1.5 | 1.0 | 0.6 | 77.7 | 15.1 | 7.0 |

A: dimethyl ether;
B: ethylene oxide;
C: 1,4-dioxane
D: others which are same with Table 1
(*1) DAIYA ION WK-20 (Trademark of Mitsubishi Kasei Co., Ltd.)
(*2) DAIYA ION PK-228 (Trademark of Mitsubishi Kasei Co., Ltd.)

EXAMPLE 64

Example 50 was repeated except that molar ratio of lactic acid/stannic chloride was 2/1. The result is shown in Table 15.

TABLE 15

| Conversion (%) | | Selectivity (based on ethylene oxide) (%) | | | | | | | | | | | |
|---|---|---|---|---|---|---|---|---|---|---|---|---|---|
| | | CH₃O—(CH₂CH₂O)ₙ—CH₃ | | | | | | | | | | | |
| A | B | n = 1 | 2 | 3 | 4 | 5 | 6 | 7 | 8 | 9 | Total | C | D |
| 49.4 | 99.3 | 29.9 | 19.8 | 13.5 | 6.8 | 4.7 | 2.7 | 1.6 | 0.8 | 0.3 | 80.2 | 12.5 | 7.3 |

A: dimethyl ether;
B: ethylene oxide;
C: 1,4-dioxane;
D: others which are same with Table 1.

EXAMPLE 65 AND COMPARISON EXAMPLE 9

Into a 500 ml four necked flask equipped with a stirrer, a condenser, a thermometer and a dropping funnel, were charged 1 mole (90 g) of ethylene glycol dimethyl ether, 0.03 moles of stannic chloride, and 0.03 moles of lactic acid for Example 65 but without adding lactic acid for Comparison Example 9. To the charged materials, 0.5 moles (46.3 g) of epichlorohydrin was dropped under stirring at 50° C. The results are shown in Table 16.

TABLE 16

| Example & Comparison Example | Conversion (%) | | Selectivity (based on epichlorohydrin) (%) | | | | | | |
|---|---|---|---|---|---|---|---|---|---|
| | | | CH₃O—(CH₂CH₂O)—(CHCH₂O)ₙ—CH₃ (*) (%)<br>$\quad\quad\quad\quad\quad\quad\quad\quad\quad\quad$CH₂Cl | | | | | | |
| | A | B | n = 1 | 2 | 3 | 4 or more | Total | C | |
| Example 65 | 40.6 | 98.0 | 66.0 | 17.9 | 5.8 | 0.4 | 90.1 | 4.9 | |
| Comp. Ex. 9 | 38.4 | 97.8 | 62.1 | 17.0 | 5.5 | 1.0 | 85.6 | 9.6 | |

A: ethylene glycol dimethyl ether;
B: epichlorohydrin;
C: 2,5-dichloromethyl-1,4-dioxane (*) The expression ignores the order of —(CH₂CH₂O)— and —(CHCH₂O)—.
$\quad\quad\quad\quad\quad\quad\quad\quad\quad\quad\quad\quad\quad\quad\quad\quad\quad\quad\quad\quad$CH₂Cl

EXAMPLES 66 AND 67 AND COMPARISON was carried out at 30° C. The results shown in Table 17.

TABLE 17

| Example & Comparison Example | Kind and amount of catalyst, mole % of (A) | Molar ratio B/A | Conversion (%) | | Selectivity (%) (*1) | | |
|---|---|---|---|---|---|---|---|
| | | | A | B | Glycol (*2) dimethyl ethers | 1,4-Dioxane | Others |
| Example 66 | BF₃.OMe₂ (0.4) + Amyl alcohol (0.4) | 0.2 | 17.3 | 99.7 | 88.7 | 11.0 | 0.4 |
| Comp. Ex. 10 | BF₃.OMe₂ (0.4) | 0.2 | 16.0 | 99.8 | 85.2 | 14.6 | 0.1 |
| Example 67 | SnCl₄ (0.4) + Lactic acid (0.4) | 2.5 | 69.1 | 99.3 | 82.1 | 14.3 | 3.6 |
| Comp. Ex. 11 | SnCl₄ (0.4) | 2.5 | 67.2 | 99.4 | 73.0 | 25.1 | 1.9 |

(*1) Based on ethylene oxide.
(*2) A mixture of mono- and poly-glycol dimethyl ethers.

EXAMPLES 68–72 AND COMPARISON EXAMPLE 12

Into a 100 ml pressure autoclave, were charged 10 g of chlorobenzene, respective active-hydrogen compound indicated in Table 18 and stannic chloride in their amounts of 1.0 mole % on the basis of dimethyl ether, and to the charged materials were added 10.5 g of dimethyl ether and 10.1 g of ethylene oxide. Reactions were conducted at 25° C. for 1.5 hours. The results are shown in Table 18.

TABLE 18

| Example & Comparison Example | Active-hydrogen Compound | Weight of reaction product (g) | Composition (%) | | Composition of diether formed (%) (*1) | | | |
|---|---|---|---|---|---|---|---|---|
| | | | Glycol diether | 1,4-Dioxane | n = 1 | 2 | 3 | 4 or more |
| Example 68 | Methanol | 10.8 | 68.2 | 18.8 | 26.2 | 18.9 | 12.6 | 42.3 |
| Example 69 | Amyl alcohol | 10.6 | 56.8 | 16.8 | 33.3 | 21.2 | 12.5 | 33.1 |
| Example 70 | sec-Butanol | 10.0 | 58.0 | 24.0 | 29.9 | 19.6 | 12.1 | 38.4 |
| Example 71 | Phenol | 10.3 | 56.7 | 27.3 | 24.1 | 17.8 | 12.0 | 46.1 |
| Example 72 | Water | 10.4 | 60.2 | 22.7 | 22.2 | 17.1 | 12.8 | 47.9 |
| Comp. Ex. 12 | None | 10.5 | 66.5 | 30.0 | 26.5 | 17.4 | 13.5 | 42.6 |

(*1) CH₃O—(CH₂CH₂O)ₙ—CH₃

EXAMPLES 10 AND 11

Example 1 was repeated except that kinds and amounts of catalysts and molar ratios of ethylene oxide (B) to dimethyl ether (A) were varied, and the reaction

What we claim is:

1. A process for the production of glycol diethers, wherein a chain-type ether compound represented by the formula $$R^1O+(CH_2)_m-O]_nR^2$$

wherein
R$^1$ is an alkyl having 1 to 4 carbon atoms,
R$^2$ is an alkyl having 1 to 12 carbon atoms, phenyl, phenyl substituted by lower alkyl or lower alkoxy, or aralkyl consisting of lower alkylene and phenyl,
m is an integer from 1 to 4, and
n is an integer from 0 to 8
and an alkylene oxide compound selected from the group consisting of compounds represented by the formulas

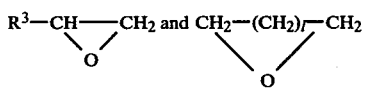

wherein
R$^3$ is halogen-or non-substituted alkyl having 1 to 5 carbon atoms or phenyl, and
l is an integer from 0 to 5
are reacted in the presence of a catalyst prepared by mixing boron trifluoride and/or stannic chloride with an active-hydrogen compound selected from the group consisting of water, alcohol carboxylic acid, phenol and sulfonic acid with the proviso that mercaptan and hydroxamic acid may be included in the said active-hydrogen compound when boron trifluoride is employed, one equivalent of the said active-hydrogen compound being mixed with 1 to 5 moles of boron trifluoride and/or stannic compound, to form a boron trifluoride and/or stannic chloride complex therewith, the said catalyst being employed in an amount of from 0.05 to 5 mole percent of the chain-type ether compound based on boron trifluoride and/or stannic chloride, and the molar ratio of the alkylene oxide compound to the chain-type ether compound is from 0.5 to 5.

2. A process according to claim 1, wherein the active-hydrogen compound is water or an aliphatic alcohol having 1 to 4 carbon atoms.

3. A process according to claim 1, wherein the chain-type ether compound is represented by the formula $$R^1O+(CH_2)_m O]_n R^2$$

wherein
R$^1$ and R$^2$ are same or different alkyl having 1 to 4 carbon atoms,
m is 1 or 2, and
n is an integer from 0 to 4.

4. A process according to claim 3, wherein
R$^1$ and R$^2$ are methyl,
m is 1, and
n is 0 or 1.

5. A process according to claim 1, wherein the alkylene oxide compound is ethylene oxide or epichlorohydrin.

6. A process according to claim 1, wherein the active-hydrogen compound is mixed with in an amount of 1 to 3 per mole of boron trifluoride and/or stannic chloride on the basis of the number of active-hydrogen.

* * * * *